United States Patent
Wang et al.

(10) Patent No.: US 7,244,603 B2
(45) Date of Patent: Jul. 17, 2007

(54) PURIFIED HPYC1I AND ITS USE AS A RESTRICTION ENDONUCLEASE

(75) Inventors: Jin-Town Wang, Taipei (TW); Tzu-Lung Lin, Taipei (TW)

(73) Assignee: National Taiwan University (TW)

( * ) Notice: Subject to any disclaimer, the term of this patent is extended or adjusted under 35 U.S.C. 154(b) by 228 days.

(21) Appl. No.: 10/796,669

(22) Filed: Mar. 9, 2004

(65) Prior Publication Data

US 2005/0202443 A1    Sep. 15, 2005

(51) Int. Cl.
| | |
|---|---|
| *C12N 9/16* | (2006.01) |
| *C12N 15/00* | (2006.01) |
| *C12N 5/02* | (2006.01) |
| *C12N 1/20* | (2006.01) |
| *C07K 14/00* | (2006.01) |
| *C07H 21/04* | (2006.01) |
| *C12Q 1/44* | (2006.01) |
| *C12P 21/06* | (2006.01) |

(52) U.S. Cl. .................. 435/196; 435/19; 435/69.1; 435/320.1; 435/325; 435/252.3; 530/350; 536/23.2

(58) Field of Classification Search ............... 435/196, 435/19, 320.1, 252.3, 325, 69.1; 530/350; 536/23.2
See application file for complete search history.

(56) References Cited

U.S. PATENT DOCUMENTS

| | | | | |
|---|---|---|---|---|
| 6,133,009 A | * | 10/2000 | Morgan et al. | ............. 435/199 |
| 6,194,188 B1 | * | 2/2001 | Morgan et al. | ............. 435/199 |
| 6,238,901 B1 | * | 5/2001 | Morgan et al. | ............. 435/193 |
| 6,238,904 B1 | * | 5/2001 | Morgan et al. | ............. 435/199 |
| 6,258,583 B1 | * | 7/2001 | Morgan et al. | ............. 435/199 |
| 6,280,992 B1 | * | 8/2001 | Morgan et al. | ............. 435/199 |

OTHER PUBLICATIONS

Aras, R.A,., et al. (2001) Mol. Microbiol. 42(2), 369-382.*
Lin, T-L, et al. (2004 J. Biol. Chem. 279(12), 11156-11162.*

* cited by examiner

*Primary Examiner*—Delia M. Ramirez
(74) *Attorney, Agent, or Firm*—Ostrolenk, Faber, Gerb & Soffen, LLP

(57) ABSTRACT

Disclosed is a novel type II restriction endonuclease. Such enzyme recognizes a particular non-palindromic sequence of 5 oligonucleotides and cleaves DNA downstream of the DNA recognition sequence of nucleotides at the fourth base in the upper strand and the fifth base in the lower strand, and forms a one-base protruding end in the 5'-end after cleavage. The recognition and cleavage site of HpyC1I is identical to the known restriction endonuclease BccI respectively, but the nucleotide sequence and the amino acid sequence are different from any other know restriction enzymes.

11 Claims, 4 Drawing Sheets

SEQUENCE LISTING

<160> NUMBER OF SEQ ID NOS: 5

<210> SEQ ID NO 1
<211> LENGTH: 5
<212> TYPE: DNA
<213> ORGANISM: Helicobacter pylori

<400> SEQUENCE: 1 ccatc                                                                      5

<210> SEQ ID NO 2
<211> LENGTH: 1617
<212> TYPE: DNA
<213> ORGANISM: Helicobacter pylori
<220> FEATURE:
<221> NAME/KEY: CDS
<222> LOCATION: (1)..(1617)

<400> SEQUENCE: 2

```
atg act aaa aaa ccg gca cga aaa att tta agc ttt tca acc acc atg        48
Met Thr Lys Lys Pro Ala Arg Lys Ile Leu Ser Phe Ser Thr Thr Met
1               5                   10                  15 cga aac cct aaa aga ata gga caa ttt tta gct gtt tta gga aag ttt        96
Arg Asn Pro Lys Arg Ile Gly Gln Phe Leu Ala Val Leu Gly Lys Phe
            20                  25                  30 gaa aat caa atc ctt aaa tct tca ata atc atg caa att atc aaa tcc       144
Glu Asn Gln Ile Leu Lys Ser Ser Ile Ile Met Gln Ile Ile Lys Ser
        35                  40                  45 gtt ttg gct cat agg ctt tat aga cct act tct ctc aat caa aat aaa       192
Val Leu Ala His Arg Leu Tyr Arg Pro Thr Ser Leu Asn Gln Asn Lys
50                  55                  60 gaa ttg aaa gaa aaa ttt gac tcc aat gaa tat gtc ttt agc gat gaa       240
Glu Leu Lys Glu Lys Phe Asp Ser Asn Glu Tyr Val Phe Ser Asp Glu
65                  70                  75                  80 gag tta gaa cgc att ata gaa ata tcc cca caa aat cat aaa gaa atg       288
Glu Leu Glu Arg Ile Ile Glu Ile Ser Pro Gln Asn His Lys Glu Met
                85                  90                  95 ggc ttt gag cat gga tgg gaa agc cgg ttt gac act tgg tat aag ctt       336
Gly Phe Glu His Gly Trp Glu Ser Arg Phe Asp Thr Trp Tyr Lys Leu
            100                 105                 110 atg tgt gag ttt ggt ttt tgc tac tat gca aaa tat gag aaa ata ctc       384
Met Cys Glu Phe Gly Phe Cys Tyr Tyr Ala Lys Tyr Glu Lys Ile Leu
        115                 120                 125 atc agc gat agc gct aag atg ctt att ctt gct tat tac aat aaa gaa       432
Ile Ser Asp Ser Ala Lys Met Leu Ile Leu Ala Tyr Tyr Asn Lys Glu
130                 135                 140
```

```
aac gat gct ttt aaa gaa agc gtt gat gaa agc gta gtt ggg gct ata        480
Asn Asp Ala Phe Lys Glu Ser Val Asp Glu Ser Val Val Gly Ala Ile
145                 150                 155                 160 ttt tta aac gct ctg tct aaa tat gaa gta gga aac cct tac aaa aag        528
Phe Leu Asn Ala Leu Ser Lys Tyr Glu Val Gly Asn Pro Tyr Lys Lys
                165                 170                 175 aat tta aac cat aac aac cct ttc aaa cta ttg ctc tcg ctt tta aaa        576
Asn Leu Asn His Asn Asn Pro Phe Lys Leu Leu Leu Ser Leu Leu Lys
            180                 185                 190 cga ctc aaa aat gcc cat cta acc ccc cta tct gtc aaa gaa atc cct        624
Arg Leu Lys Asn Ala His Leu Thr Pro Leu Ser Val Lys Glu Ile Pro
        195                 200                 205 att tta ctt tgt tgg aaa gac gat aac gct aat ggg ctt tat gac tac        672
Ile Leu Leu Cys Trp Lys Asp Asp Asn Ala Asn Gly Leu Tyr Asp Tyr
    210                 215                 220 att att cgt tta aga caa gaa atc gtt act atc aat aaa aca gaa ttc        720
Ile Ile Arg Leu Arg Gln Glu Ile Val Thr Ile Asn Lys Thr Glu Phe
225                 230                 235                 240 agc tac tca gat gaa ttt atc tat gaa aaa tgc cta aaa ctt tta gaa        768
Ser Tyr Ser Asp Glu Phe Ile Tyr Glu Lys Cys Leu Lys Leu Leu Glu
                245                 250                 255 agt gtt aat aaa aca cga ttt aaa atg agc caa atc act aac gaa gcc        816
Ser Val Asn Lys Thr Arg Phe Lys Met Ser Gln Ile Thr Asn Glu Ala
            260                 265                 270 gtt gat gaa tac att aga aaa atg cgt att aca gga ctt att tca ttg        864
Val Asp Glu Tyr Ile Arg Lys Met Arg Ile Thr Gly Leu Ile Ser Leu
        275                 280                 285 cgt ggt aat ggt agg ttt att gat att aat act aat gaa aat aat aaa        912
Arg Gly Asn Gly Arg Phe Ile Asp Ile Asn Thr Asn Glu Asn Asn Lys
    290                 295                 300 ata gat tac att tta caa acc cat aag gct ttt aaa ggg gat tat tta        960
Ile Asp Tyr Ile Leu Gln Thr His Lys Ala Phe Lys Gly Asp Tyr Leu
305                 310                 315                 320 aac gac act caa gct aac aaa ctc gcc ttt ttt aac tac atg gcg atc       1008
Asn Asp Thr Gln Ala Asn Lys Leu Ala Phe Phe Asn Tyr Met Ala Ile
                325                 330                 335 gtg gat agc ttt ctt gtt agt gtt act cca atc agc gct aat gag agc       1056
Val Asp Ser Phe Leu Val Ser Val Thr Pro Ile Ser Ala Asn Glu Ser
            340                 345                 350 gtt aaa tca agc aaa ttg aat gaa cta gca aac act tat act aaa gat       1104
Val Lys Ser Ser Lys Leu Asn Glu Leu Ala Asn Thr Tyr Thr Lys Asp
        355                 360                 365 ttt atc aag caa gaa tta ctc att act tgt aac aag caa gaa tca aaa       1152
Phe Ile Lys Gln Glu Leu Leu Ile Thr Cys Asn Lys Gln Glu Ser Lys
    370                 375                 380 gat agt ttt tta aga ctc att gat aaa cct tta cgc tta gaa ttt tta       1200
Asp Ser Phe Leu Arg Leu Ile Asp Lys Pro Leu Arg Leu Glu Phe Leu
385                 390                 395                 400 agc gct att ttc ttg aaa caa cat ttt gaa aat tta agc gtg ata ccc       1248
Ser Ala Ile Phe Leu Lys Gln His Phe Glu Asn Leu Ser Val Ile Pro
                405                 410                 415 aat tat aaa agc gat gat gaa ggc ttg ccc gta tac aca gca agc ggt       1296
Asn Tyr Lys Ser Asp Asp Glu Gly Leu Pro Val Tyr Thr Ala Ser Gly
            420                 425                 430 aat aaa cct gat att gta gct atg gac aca aaa gcc caa agt tat ata       1344
Asn Lys Pro Asp Ile Val Ala Met Asp Thr Lys Ala Gln Ser Tyr Ile
        435                 440                 445 gaa gtg agc ttg att aga gac aga agt caa agt acc ttg gaa atg ata       1392
Glu Val Ser Leu Ile Arg Asp Arg Ser Gln Ser Thr Leu Glu Met Ile
```

-continued

```
               450                 455                 460
cct att gcc aga cat tta aaa gaa ttg att aaa aat agc acc gat att      1440
Pro Ile Ala Arg His Leu Lys Glu Leu Ile Lys Asn Ser Thr Asp Ile
465                 470                 475                 480 aga gaa aaa ttt agt gtt ttt gta gct cca aat atc cat gat gat gcc      1488
Arg Glu Lys Phe Ser Val Phe Val Ala Pro Asn Ile His Asp Asp Ala
                    485                 490                 495 aaa gaa tat gcg gaa ttt gcc caa ttc aaa gac aat att aat ata tgt      1536
Lys Glu Tyr Ala Glu Phe Ala Gln Phe Lys Asp Asn Ile Asn Ile Cys
                500                 505                 510 tgt tat gct att aat gat ttt atc aaa aaa gta gaa aac agc ata gaa      1584
Cys Tyr Ala Ile Asn Asp Phe Ile Lys Lys Val Glu Asn Ser Ile Glu
            515                 520                 525 tgg tta cag atc aat gac cat ttg aaa gct taa                          1617
Trp Leu Gln Ile Asn Asp His Leu Lys Ala
        530                 535
```

<210> SEQ ID NO 3
<211> LENGTH: 538
<212> TYPE: PRT
<213> ORGANISM: Helicobacter pylori

<400> SEQUENCE: 3

```
Met Thr Lys Lys Pro Ala Arg Lys Ile Leu Ser Phe Ser Thr Thr Met
1               5                   10                  15

Arg Asn Pro Lys Arg Ile Gly Gln Phe Leu Ala Val Leu Gly Lys Phe
                20                  25                  30

Glu Asn Gln Ile Leu Lys Ser Ser Ile Ile Met Gln Ile Ile Lys Ser
            35                  40                  45

Val Leu Ala His Arg Leu Tyr Arg Pro Thr Ser Leu Asn Gln Asn Lys
    50                  55                  60

Glu Leu Lys Glu Lys Phe Asp Ser Asn Glu Tyr Val Phe Ser Asp Glu
65                  70                  75                  80

Glu Leu Glu Arg Ile Ile Glu Ile Ser Pro Gln Asn His Lys Glu Met
                85                  90                  95

Gly Phe Glu His Gly Trp Glu Ser Arg Phe Asp Thr Trp Tyr Lys Leu
                100                 105                 110

Met Cys Glu Phe Gly Phe Cys Tyr Tyr Ala Lys Tyr Glu Lys Ile Leu
            115                 120                 125

Ile Ser Asp Ser Ala Lys Met Leu Ile Leu Ala Tyr Tyr Asn Lys Glu
    130                 135                 140

Asn Asp Ala Phe Lys Glu Ser Val Asp Glu Ser Val Val Gly Ala Ile
145                 150                 155                 160

Phe Leu Asn Ala Leu Ser Lys Tyr Glu Val Gly Asn Pro Tyr Lys Lys
                165                 170                 175

Asn Leu Asn His Asn Asn Pro Phe Lys Leu Leu Ser Leu Leu Lys
            180                 185                 190

Arg Leu Lys Asn Ala His Leu Thr Pro Leu Ser Val Lys Glu Ile Pro
    195                 200                 205

Ile Leu Leu Cys Trp Lys Asp Asp Asn Ala Asn Gly Leu Tyr Asp Tyr
210                 215                 220

Ile Ile Arg Leu Arg Gln Glu Ile Val Thr Ile Asn Lys Thr Glu Phe
225                 230                 235                 240

Ser Tyr Ser Asp Glu Phe Ile Tyr Glu Lys Cys Leu Lys Leu Leu Glu
                245                 250                 255

Ser Val Asn Lys Thr Arg Phe Lys Met Ser Gln Ile Thr Asn Glu Ala
```

```
                260                265                270
Val Asp Glu Tyr Ile Arg Lys Met Arg Ile Thr Gly Leu Ile Ser Leu
            275                280                285
Arg Gly Asn Gly Arg Phe Ile Asp Ile Asn Thr Asn Glu Asn Asn Lys
        290                295                300
Ile Asp Tyr Ile Leu Gln Thr His Lys Ala Phe Lys Gly Asp Tyr Leu
305                310                315                320
Asn Asp Thr Gln Ala Asn Lys Leu Ala Phe Phe Asn Tyr Met Ala Ile
                325                330                335
Val Asp Ser Phe Leu Val Ser Val Thr Pro Ile Ser Ala Asn Glu Ser
            340                345                350
Val Lys Ser Ser Lys Leu Asn Glu Leu Ala Asn Thr Tyr Thr Lys Asp
        355                360                365
Phe Ile Lys Gln Glu Leu Leu Ile Thr Cys Asn Lys Gln Glu Ser Lys
370                375                380
Asp Ser Phe Leu Arg Leu Ile Asp Lys Pro Leu Arg Leu Glu Phe Leu
385                390                395                400
Ser Ala Ile Phe Leu Lys Gln His Phe Glu Asn Leu Ser Val Ile Pro
                405                410                415
Asn Tyr Lys Ser Asp Asp Glu Gly Leu Pro Val Tyr Thr Ala Ser Gly
            420                425                430
Asn Lys Pro Asp Ile Val Ala Met Asp Thr Lys Ala Gln Ser Tyr Ile
        435                440                445
Glu Val Ser Leu Ile Arg Asp Arg Ser Gln Ser Thr Leu Glu Met Ile
450                455                460
Pro Ile Ala Arg His Leu Lys Glu Leu Ile Lys Asn Ser Thr Asp Ile
465                470                475                480
Arg Glu Lys Phe Ser Val Phe Val Ala Pro Asn Ile His Asp Asp Ala
                485                490                495
Lys Glu Tyr Ala Glu Phe Ala Gln Phe Lys Asp Asn Ile Asn Ile Cys
            500                505                510
Cys Tyr Ala Ile Asn Asp Phe Ile Lys Lys Val Glu Asn Ser Ile Glu
        515                520                525
Trp Leu Gln Ile Asn Asp His Leu Lys Ala
    530                535
```

<210> SEQ ID NO 4
<211> LENGTH: 780
<212> TYPE: DNA
<213> ORGANISM: Helicobacter pylori
<220> FEATURE:
<221> NAME/KEY: CDS
<222> LOCATION: (1)..(780)

<400> SEQUENCE: 4

```
atg ggg caa gac gct gat ttt aaa gcg ctt gaa gaa ctg aaa gaa tac    48
Met Gly Gln Asp Ala Asp Phe Lys Ala Leu Glu Glu Leu Lys Glu Tyr
1               5                   10                  15 ttt aat caa gct tta aag cta gaa gaa aat tat ttt agc caa cat ttt    96
Phe Asn Gln Ala Leu Lys Leu Glu Glu Asn Tyr Phe Ser Gln His Phe
                20                  25                  30 agc aac aag ttt ttc agc tat aaa gat tgt gtc aaa atc ggt agc att   144
Ser Asn Lys Phe Phe Ser Tyr Lys Asp Cys Val Lys Ile Gly Ser Ile
            35                  40                  45 aga gag cat ata gaa agc tta aac tta gat aaa tta aat aaa gat att   192
Arg Glu His Ile Glu Ser Leu Asn Leu Asp Lys Leu Asn Lys Asp Ile
        50                  55                  60
```

-continued

```
tta tta aca agc ctg att tat tca atg gat aag ata gct aac acg gta       240
Leu Leu Thr Ser Leu Ile Tyr Ser Met Asp Lys Ile Ala Asn Thr Val
 65                  70                  75                  80 ggg cat tat gaa gct tat agg aaa aaa gag att ttg caa gat aga ttt       288
Gly His Tyr Glu Ala Tyr Arg Lys Lys Glu Ile Leu Gln Asp Arg Phe
                 85                  90                  95 att ttt gag ctt att agc cct ata aaa cat gat aaa aat atc atg ata       336
Ile Phe Glu Leu Ile Ser Pro Ile Lys His Asp Lys Asn Ile Met Ile
            100                 105                 110 gag aga aaa aac gct aac gaa ttg gct aaa acc tta aaa ata gac tta       384
Glu Arg Lys Asn Ala Asn Glu Leu Ala Lys Thr Leu Lys Ile Asp Leu
        115                 120                 125 gtc ttt att gat cct cca tac aat tca agg caa tac agc cgg ttt tat       432
Val Phe Ile Asp Pro Pro Tyr Asn Ser Arg Gln Tyr Ser Arg Phe Tyr
    130                 135                 140 cat ctc tat gaa aac cta gtg cag tgg aaa aaa ccc aaa ctc tat gga       480
His Leu Tyr Glu Asn Leu Val Gln Trp Lys Lys Pro Lys Leu Tyr Gly
145                 150                 155                 160 aca gct tta aag cca tca tgc gag aac atg agc gaa tat tgc cgc tct       528
Thr Ala Leu Lys Pro Ser Cys Glu Asn Met Ser Glu Tyr Cys Arg Ser
                165                 170                 175 aat gcc aag aaa gaa ttg agc gat tta att gaa aaa cta gat tgt aaa       576
Asn Ala Lys Lys Glu Leu Ser Asp Leu Ile Glu Lys Leu Asp Cys Lys
            180                 185                 190 agg att gct tta act tat aat aat acc tat aac tct aag tct agc tct       624
Arg Ile Ala Leu Thr Tyr Asn Asn Thr Tyr Asn Ser Lys Ser Ser Ser
        195                 200                 205 tcg caa aat aaa ata ggc ttt aaa gat tta gtg gaa att ttg agt caa       672
Ser Gln Asn Lys Ile Gly Phe Lys Asp Leu Val Glu Ile Leu Ser Gln
    210                 215                 220 aaa gga aaa tta agc gtt aaa gaa aag gct cat agt ttt ttt aat tca       720
Lys Gly Lys Leu Ser Val Lys Glu Lys Ala His Ser Phe Phe Asn Ser
225                 230                 235                 240 gga aaa act gat ttt aaa gag cat aaa gaa ttt tta ttt ata gtg gaa       768
Gly Lys Thr Asp Phe Lys Glu His Lys Glu Phe Leu Phe Ile Val Glu
                245                 250                 255 gtg aaa cct tga                                                       780
Val Lys Pro <210> SEQ ID NO 5
<211> LENGTH: 846
<212> TYPE: DNA
<213> ORGANISM: Helicobacter pylori
<220> FEATURE:
<221> NAME/KEY: CDS
<222> LOCATION: (1)..(846)

<400> SEQUENCE: 5 atg cca caa ctc aat aag cta ttc cca aat aac att aat caa ttt att        48
Met Pro Gln Leu Asn Lys Leu Phe Pro Asn Asn Ile Asn Gln Phe Ile
 1               5                  10                  15 gag cct ttt gtg ggt ggg ggt agc gtg ttt tta aac act aag gct aag        96
Glu Pro Phe Val Gly Gly Gly Ser Val Phe Leu Asn Thr Lys Ala Lys
                 20                  25                  30 aga tac tta gct aat gac ata gat act aat att atc aat tta cat aaa       144
Arg Tyr Leu Ala Asn Asp Ile Asp Thr Asn Ile Ile Asn Leu His Lys
            35                  40                  45 act tta agc aag ttc aat gtt tgt gag ctt ttt gat gaa ttg tct aaa       192
Thr Leu Ser Lys Phe Asn Val Cys Glu Leu Phe Asp Glu Leu Ser Lys
        50                  55                  60
```

-continued

```
att atc att cat tat ggc ttg tct ttc tct ttt aag ggg att atg gcc        240
Ile Ile Ile His Tyr Gly Leu Ser Phe Ser Phe Lys Gly Ile Met Ala
 65              70                  75                  80 cct gat gaa tta aaa aaa caa tat ata aaa act tac tac gcc aaa tac        288
Pro Asp Glu Leu Lys Lys Gln Tyr Ile Lys Thr Tyr Tyr Ala Lys Tyr
                 85                  90                  95 aat aaa ata gct tat gaa aaa cta agg gct gat ttt aac tcc aat caa        336
Asn Lys Ile Ala Tyr Glu Lys Leu Arg Ala Asp Phe Asn Ser Asn Gln
            100                 105                 110 aac aac atg ctt tat ttg tat ttg ctt tta att tat gga ttt aat cac        384
Asn Asn Met Leu Tyr Leu Tyr Leu Leu Leu Ile Tyr Gly Phe Asn His
        115                 120                 125 atg att aga ttt aat tct aaa ggg ctt ttt aat tta cct gtg ggt aat        432
Met Ile Arg Phe Asn Ser Lys Gly Leu Phe Asn Leu Pro Val Gly Asn
    130                 135                 140 gtg gat ttc aat gaa aat gtt tat aat gcc cta aaa aac tac ata gat        480
Val Asp Phe Asn Glu Asn Val Tyr Asn Ala Leu Lys Asn Tyr Ile Asp
145                 150                 155                 160 ttt ata cag caa aac acc att att ttt cac aat gat gat tat att gat        528
Phe Ile Gln Gln Asn Thr Ile Ile Phe His Asn Asp Asp Tyr Ile Asp
                165                 170                 175 ttt ctt aac cac acc act tat tta aaa gat gat tat gtt tat ttt gac        576
Phe Leu Asn His Thr Thr Tyr Leu Lys Asp Asp Tyr Val Tyr Phe Asp
            180                 185                 190 ccc cct tat tta atc tcc aat agt gaa tac aac aag tta tgg gat agc        624
Pro Pro Tyr Leu Ile Ser Asn Ser Glu Tyr Asn Lys Leu Trp Asp Ser
        195                 200                 205 gat aat gag ata gcc tta tat ggt gtt tta gat agc cta gat aaa aag        672
Asp Asn Glu Ile Ala Leu Tyr Gly Val Leu Asp Ser Leu Asp Lys Lys
    210                 215                 220 gga gtt tta ttt ggt ata act aat ctt att tat cac aag gga gag act        720
Gly Val Leu Phe Gly Ile Thr Asn Leu Ile Tyr His Lys Gly Glu Thr
225                 230                 235                 240 aat ttt att tta aaa gaa tgg gct aaa aaa tat tat att ttt aat atc        768
Asn Phe Ile Leu Lys Glu Trp Ala Lys Lys Tyr Tyr Ile Phe Asn Ile
                245                 250                 255 aaa agt aat tat atc agt tat aat gac aat act att aaa gaa gat agt        816
Lys Ser Asn Tyr Ile Ser Tyr Asn Asp Asn Thr Ile Lys Glu Asp Ser
            260                 265                 270 caa gaa atc ttt gta act aat tat agg tga                                846
Gln Glu Ile Phe Val Thr Asn Tyr Arg
        275                 280
```

PURIFIED HPYC1I AND ITS USE AS A RESTRICTION ENDONUCLEASE

BACKGROUND OF THE INVENTION

1. Field of the Invention

The present invention relates to a DNA-cutting enzyme, especially relates to a novel type II restriction endonuclease which recognizes and cuts DNA only at a particular sequence of nucleotides.

2. The Prior Arts

Restriction endonuclease is one of DNA-cutting enzymes found in bacteria. A restriction enzyme recognition sequence containing a two fold axis of symmetry. Therefore the recognition sequences from the 5'-end to the 3'-end are the same on either upper strand or lower strand of DNA duplex, and such symmetry is termed palindrome. For the nomenclature of restriction enzymes, the first 3 letters of the name refer to a strain of bacterium, which bacterium is the source of the enzyme, the following letter indicates the particular strain, and the last part of the name is a Roman numeral which indicates the order of discovery. For example, EcoRI was isolated from *Escherichia coli* (strain RY13).

Traditionally, the restriction endonucleases are divided into 3 groups, designated type I, type II and type III according to domain structure, cleavage position, specificity of recognition sequence, and cofactors requirements. Type I and type II enzymes are similar in that both have restriction endonuclease and methylase activities. Type I restriction enzymes bind to the recognition site and then cut randomly, somewhere thousand of bases from the recognition sequence. Type III enzymes cleave DNA around 24 to 26 bases along the length of the molecule. Type II restriction enzymes are found in late 1960's by Hamilton Smith et al., which recognize and cut DNA only at a particular sequence of nucleotides. Generally speaking, type II restriction enzymes recognize a specific sequence with 4 to 8 base pairs in length in double stranded deoxyribonucleic acid (DNA), and cleave specific site of the double helix DNA. Each restriction enzyme recognizes a specific sequence of nucleotide bases and cleaves the DNA along the molecule. Bacteria prevent their own DNA from being degraded by methylating their recognition sequences, which sequences are thus modified and protected from the endonucleases. The specific cleavage sites of restriction enzyme are close to the recognition sequences, and therefore restriction enzymes that recognize different nucleotide sequences can be purified from different bacterial species. They function like genetic scissors which allow DNA to be cut at desired sites and therefore become powerful tools in genetic or molecular manipulation.

The restriction enzyme and its corresponding methylase constitute the restriction-modification system (R-M) of a bacterial species. R-M system in bacteria protects against invasion of foreign DNA. The restriction endonuclease recognizes a specific sequence and the cognate methyltransferase modifies the same sequence to differentiate self-DNA from foreign DNA. Thousands of restriction enzymes have been purified and characterized.

Because of the abovementioned properties, the use of restriction enzymes are broadly applied in genetic engineering, DNA or gene cloning and gene mapping.

There are more than 20 putative R-M systems discovered in *H. pylori* 26695 and J99 strains based on sequence homology. Previous studies show that there are 14 Type II R-M systems with biochemical activities in *H. pylori* 26695 strain. The R-M systems of these two strains are very different when the complete sequences of 26695 and J99 strains are compared. The difference of R-M systems results in the barrier of interstrain plasmid DNA transfer and chromosomal DNA transformation. The biological significance of such diverse and complicated R-M systems in *H. pylori* is still unclear.

Isoschizomer are restriction enzymes that recognize the same sequence. However, the isoschizomers from different sources showed various sensitivities to different modified DNA. Therefore, several restriction enzymes from different sources but cutting the sequence at the same location will be employed together to obtain a better cleavage effect in the target nucleotide sequence.

The present invention therefore provides a restriction enzyme which can specifically recognize and cut a particular nucleotide sequence in order to provide alternative choices for cleaving DNA in the biotechnological manipulation of genetic engineering and gene cloning, and to improve the cutting efficiency. In addition, it offers a better cleavage effect for target nucleotide sequences which can not be efficiently cut with known restriction endonucleases.

SUMMARY OF THE INVENTION

The primary object of the present invention is to provide a novel type II restriction endonuclease which recognizes and cuts DNA only at a particular sequence of nucleotides.

Such novel type II restriction enzyme is obtained from R-M system of a *Helicobacter pylori* strain which is publicly deposited as CCRC17132 in Culture Collection and Research Center of Food Industry Research and Development Institute (Taiwan) on Feb. 12, 2001.

Using transposon shuttle mutagenesis of *H. pylori* (CCRC17132) allows the identification of different mutant strains. Cell adherence assay is employed thereafter to screen low adherence of these mutant strains. Mutants exhibiting decreased adherences are observed under a microscope. Light microscopic observation reveals a significant elongated morphology, as shown in FIG. 1.

The DNA sequences for each of the mutants are determined with conventional inverse polymerase chain reaction and sequence analysis. The same locus in these six mutant strains is interrupted by a transposon gene. Nucleotide and amino acid sequences show no homologies with the published sequences of *H. pylori* 26695 and J99 strains.

This transposon gene comprises a novel open reading frame (ORF) which contains 1617 base pairs (SEQ ID NO: 2) and encodes a peptide of 538 amino acids (SEQ ID NO: 3). The amino acid sequence SEQ ID NO: 3 shares 24% identity with a putative nicking enzyme of *Bacillus halodurans*. In addition, SEQ ID NO: 3 is homologous to the known type II restriction endonucleases PleI and MlyI with 23% and 20% identity respectively.

The 1617 base pairs of sequence SEQ ID NO: 2 is expressed with conventional methods of protein expression, and purified through conventional purification methods. The protein obtained is termed HpyC1I, and the number is designated SEQ ID NO:3. The purified protein, HpyC1I, shows endonuclease activity with a non-palindromic recognition sequence of 5'-CCATC-3' (designated SEQ ID NO: 1) and cleaves the fourth base downstream from the recognition sequence of the upper strand and the fifth base from that of the lower strand of SEQ ID NO: 1. The recognition and cleavage site of HpyC1I is identical to those of the known restriction endonuclease BccI respectively after comparison. This result shows that HpyC1I is an isoschizomer of BccI.

On the other hand, two ORFs are located upstream of the gene encoding HpyC1I after further analysis. HpyC1I and these two putative methyltransferases (M1.HpyC1I and M2.HpyC1I) function together to compose a restriction-modification (R-M) system to protect *H. pylori* CCRC17132 from invasion of foreign DNA.

The present invention will be further explained in the following embodiment illustration and examples. However, the present invention is not limited to these examples. The present invention may be altered or modified and all such variations are considered within the scope and spirit of the present invention.

DETAILED DESCRIPTION OF THE PREFERRED EMBODIMENT

Example 1

Screening Mutants with Adherence Assay

Conventional transposon (mini-TnKm) shuttle mutagenesis is employed in a clinical isolate *H. pylori* CCRC17132 to obtain mutant strains. A total of 1500 *H. pylori* mutant strains are obtained.

To identify the adherence of mutant strains, 24-well culture plates are used to screen each of the mutant strains in duplicate. SC-M1 used in this study, is a cell line established from primary human gastric cancer tissue. This cell line is proved to be $Le^b$ negative and $sLe^x$ positive by monoclonal antibodies against $Le^b$ (Seikagaku, Tokyo, Japan) and $sLe^x$ (Chemicon, Temecula, Calif.) respectively.

First of all, the SC-M1 cells are grown in RPMI 1640 medium (Gibco BRL, Rockville, Md.) supplemented with 10% fetal calf serum (FCS). The cells are plated in 24-well culture plates and grown in a humidified atmosphere at 37° C. with 5% $CO_2$. Infections are performed to the cells by adding *H. pylori* at a multiplicity of infection (MOI) of 100. After 30 minutes of co-cultivation at 37° C., non-adherent bacteria are removed with PBS buffer washing for three times. SC-M1 cells with adherent *H. pylori* are trypsinized, serially diluted in normal saline, and spread on the Columbia blood agar plates. Recovered adherent bacterial colonies are counted. Wild type CCRC17132 strain is served as a positive control, and the adherent ability of each mutant strain is compared to that of the wild type strain.

Figure 2:
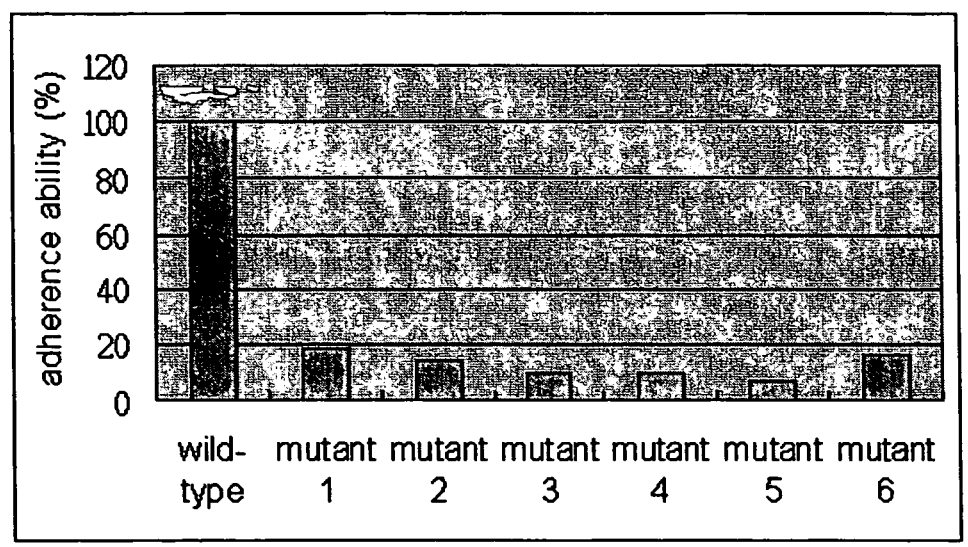
FIG. 2 shows adherent ability of wild type and mutant strains of *H. pylori* CCRC17132, wherein the adherent ability is expressed as a percentage in comparison to wild type (taken as 100%). The values are means of triplicate data.

Six mutant strains are obtained, which are co-cultivated with SC-M1 cells for 30 min. These six mutant strains reveal a 5 to 10-fold decrease of the recovered adherent bacteria counts compared to those of wild type strain (FIG. 2).

The morphologies of *H. pylori* wild type and mutant strains are observed with a light microscope after Gram staining and recorded by CoolSnap-pro software (Media Cybernetics, Silver Spring, Md.). More than ten fields are examined on each slide and the lengths of bacteria are measured in 30 bacteria of 5-10 different fields by CoolSnap-pro software (Media Cybernetics).

Figure 1:
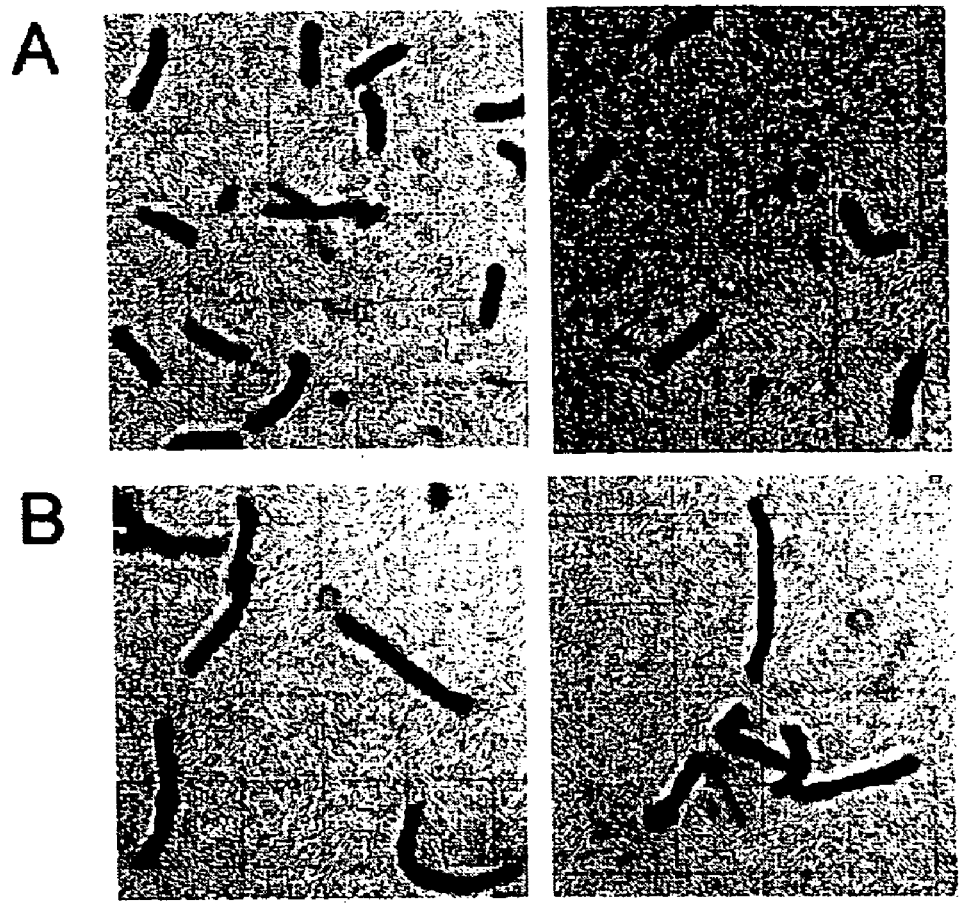
FIG. 1 shows a comparison of morphology of wild type and mutant strains of *H. pylori* CCRC17132 observed with a light microscope at high magnification (1,000×) after Gram staining, wherein A is wild type and B is mutant strains.

Light microscopic observation reveals elongation of the mutant strains (FIG. 1). The lengths of wild type strain are 4.3±0.82 µm and those of the mutant strains are 8.7±1.50 µm in average. Therefore, the decreased adherent ability might due to abnormal appearance or other indirect effects.

Example 2

Identification of Inserted Gene with Inverse PCR and DNA Sequencing

To identify genetic loci interrupted by the transposon, genomic DNA of mutant strains are extracted and subjected to inverse PCR and DNA sequencing analysis. The mini-TnKm insertion site for each of the mutants is determined and compared with the NCBI BLAST databases (ncbi.nlm.nih.gov/BLAST) as well as the *H. pylori* genome database (tigr.org).

Results show that these six mutant strains are interrupted by the mini-TnKm at the same locus. The transposon insertion site of these six mutants is at the 773th nucleotide of this locus. This transposon gene comprises a novel open reading frame (ORF) which contains 1617 base pairs (SEQ ID NO :2). The nucleotide and amino acid sequences show no homologies with the published sequences of *H. pylori* 26695 and J99 strains. The amino acid sequence SEQ ID NO : 3 encoded by SEQ ID NO : 2 is compared with NCBI BLAST databases. The amino acid sequence shows 24% identity with a putative nicking enzyme in *Bacillus halodurans*, and 23% and 20% identity with two Type II restriction endonucleases PleI and MlyI, respectively.

Figure 3:
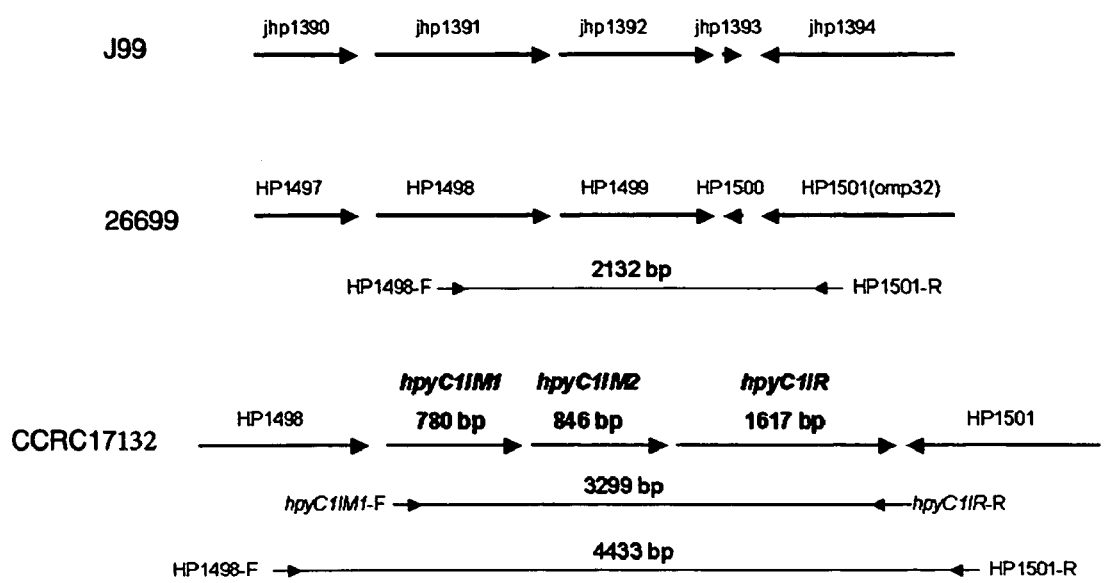
FIG. 3 shows gene arrangement of R-M system from wild type and mutant strains of *H. pylori* CCRC17132, and the relative areas from *H. pylori* 26695 and J99 strains, wherein arrows represent position and orientation of open reading frame. The figure is illustrated but not according to percentage of a real size. The name and the size of each locus are labeled above the arrows.

There are two ORFs located upstream of SEQ ID NO : 2 after further analysis. Both the upstream ORFs contain a methyltransferase domain, with 780 base pairs and 846 base pairs in length respectively, and are termed hpyC1IM1 (SEQ ID NO : 4) and hpyC1IM2 (SEQ ID NO : 5). Based on protein function predictions and gene alignments, the present inventors propose that these 3 ORFs form an operon and function as an R-M system. This 3.3 kb DNA fragment containing SEQ ID NO : 2, SEQ ID NO : 4 and SEQ ID NO : 5 is absent in both *H. pylori* 26695 and J99 strains (FIG. 3). It has been deposited in DDBJ/EMBL/GenBank with an accession number of AB118944.

Example 3

Expression and Purification of Restriction Endonuclease

To analyze the activity of this restriction endonuclease, the hpyC1IR gene is subcloned into pET28c plasmid and expressed in *E. coli*. Purification of His-tag fusion protein is carried out under Ni-NTA agarose column chromatography.

In the beginning, the gene encoding HpyC1I SEQ ID NO : 2 is amplified by using PCR and cloned into a pGEM-T easy plasmid (Promega, Madison, Wis., USA). The resultant plasmid pGEM-T easy/hpyC1IR is then digested with NotI (New England Biolabs, Beverly, Mass.) and ligated in-frame into pET28c plasmid (Novagen, Darmstadt, Germany). The resulting pET28c/hpyC1IR. plasmid is transformed into an *E. coli* strain BL21(DE3). The HpyC1I protein is expressed under 1 mM IPTG (isopropyl-β-D-thiogalactoside) induction at room temperature. The $His^6$ tag protein is purified with a $Ni^{2+}$-NTA agarose column (Qiagen, Hilden, Germany). The enzyme activity of purified protein is determined on HpyC1I digested lambda DNA.

The endonuclease activity of purified protein HpyC1I (SEQ ID NO:3) is detected by cleavage of lambda DNA. The preferred reaction conditions are under 1× NEB buffer 1 (10 mM Bis Tris Propane-HCl, 10 mM $MgCl_2$, 1 mM DTT pH 7.0) supplemented with 100 μg/ml BSA and incubate at 37° C. About 60 ng purified protein (0.1 μl) can digest 1 μg of lambda DNA in one hour at 37° C.

Example 4

Recognition and Cleavage Site of HpyC1I

To determine the recognition and cleavage site of HpyC1I, cloning and sequencing of the HpyC1I digestion products from bacteriophage lambda DNA (New England Biolabs) are performed. The HpyC1I digested fragments are blunted by T4 DNA polymerase and cloned into the EcoRV (New England Biolabs) site of pBR322 plasmid. Because the EcoRV site of pBR322 is in the tetracycline resistance gene fragment, the $AMP^r$ (ampicillin resistant) and $Tc^s$ (tetracycline sensitive) transformants are selected. Plasmid DNA is isolated from the abovementioned colonies and 10 of the restriction fragment-vector junctions are sequenced.

Comparisons of the 10 junction sequences indicate that no sequence is the same Therefore, HpyC1I does not recognize and cut within some sequence fragments. Further analysis identifies a putative non-palindromic recognition sequence in the cloned inserts at a constant distance from the junction. Therefore, HpyC1I belongs to type II restriction endonuclease. The enzyme recognizes a 5 base-pair asymmetric sequence, 5'-CCATC-3' (SEQ ID NO:1), and cleaves DNA downstream of the recognition site, after nucleotide 4 and 5 in the upper and the lower strand respectively. These strands are more conventionally referred to as the 'top strand' and the 'bottom strand', respectively. The double-strand cleavage of HpyC1I produces a one-base 5'-protruding end as shown in Table 1.

Figure 4:
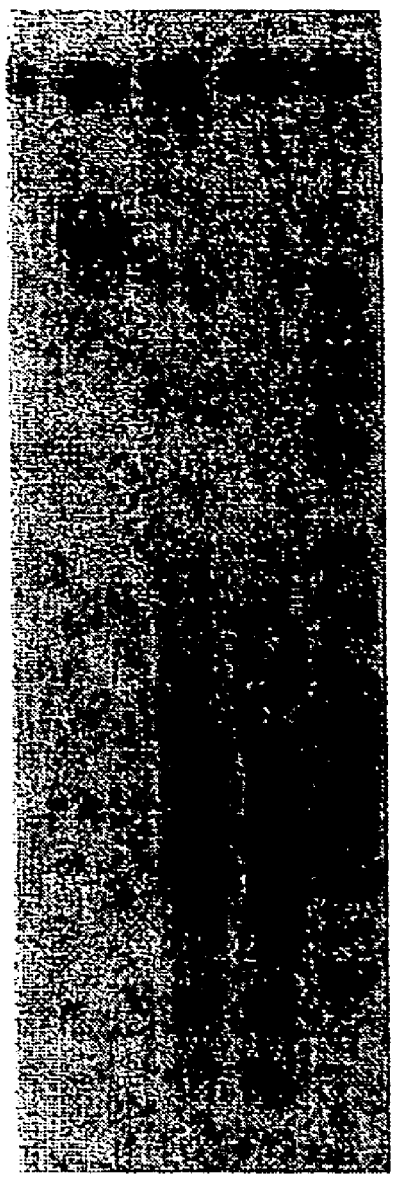
FIG. 4 shows the lambda DNA patterns after digestion with HpyC1I and BccI respectively in a 1.5% agarose gel, wherein Lane 1 is uncut lambda DNA; Lane 2 is lambda DNA digested with HpyC1I; Lane 3 is lambda DNA digested with BccI; and Lane M is 1 kb DNA marker.

In addition, searches in REBASE database (rebase.neb.com) reveal that both the recognition and cleavage sites of HpyC1I are identical to restriction endonuclease BccI. Therefore, HpyC1I is an isoschizomer of BccI. The reaction conditions, R-M genes alignment, and the HpyC1I digestion patterns of lambda, pBR322 and $phiX^{174}$ DNA are all the same with BccI (FIG. 4).

TABLE 1

Cloning and sequencing of the HpyC1I digestion products from bacteriophage lambda DNA are employed to determine the recognition and cleavage site of HpyC1I.

| Position in lambda DNA | DNA sequence around HpyC1I cleavage site of lambda DNA |
|---|---|
| 1325–1364 | 5'-*CTGGCCAAAGT*CCATC CGTG↓GCTCCACGCCAAAAGTGAGA-3' (SEQ ID NO: 6) |
| 1596–1635 | 5'-GAAAAGACCGGGATCTGGAC↓*CCGT*GATGG*CATTCTCTGGT*-3' (SEQ ID NO: 7) |
| 4797–4836 | 5'-*TGCTCGATATGGACACGCCC*↓GGCGGGATGGTGGCGGGGGC-3' (SEQ ID NO: 8) |
| 4970–5009 | 5'-CGGACAGGCTCCATCGGCGT↓*CATGATGGCTCACAGTAATT*-3' (SEQ ID NO: 9) |
| 9581–9620 | 5'-*CAGTGGTATGA*CCATC*ACCG*↓TGAACGGCGTTGCTGCAGGC-3' (SEQ ID NO: 10) |
| 9855–9894 | 5'-GTGGAAGACGCCATCAGAAC↓*CGGCGCGTTTCTGGTGGCGA*-3' (SEQ ID NO: 11) |
| 11833–11872 | 5'-*TCCTGCAGGCGGATTACAAC*↓ACGCTGATGGCGGCGGCGAA-3' (SEQ ID NO: 12) |
| 12404–12443 | 5'-TGAAGACCAGCTTCGCGGGA↓*ACTG*GATGG*CAGGCCTGAAG*-3' (SEQ ID NO: 13) |
| 39312–39351 | 5'-*AGACTATCGCA*CCATC*AGCC*↓AGAAAACCGAATTTTGCTGG-3' (SEQ ID NO: 14) |

TABLE 1-continued

Cloning and sequencing of the HpyC1I digestion products from bacteriophage lambda DNA are employed to determine the recognition and cleavage site of HpyC1I.

| Position in lambda DNA | DNA sequence around HpyC1I cleavage site of lambda DNA |
|---|---|
| 39588–39627 | 5'-ATCTATGAAAAACATCGCCG↓*CACA*GATGG*TTAACTTTGAC*-3"<br>(SEQ ID NO: 15) |

Bold letters: HpyC1I digested lambda DNA after cloning.
Italic letters: Neighboring nucleotides around the HpyC1I digested lambda DNA after cloning.
Boxed regions: Recognition site of HpyC1I enzyme.
Vertical arrows: Cleavage site of HpyC1I enzyme.

What is claimed is:

1. An isolated type II restriction endonuclease which recognizes only a particular DNA sequence for initiating DNA cleaving, wherein the enzyme comprises the amino acid sequence of SEQ ID NO: 3, and wherein the particular DNA sequence recognized by the type II restriction endonuclease comprises the sequence 5'-CCATC-3' as set forth in SEQ ID NO: 1.

2. The isolated type II restriction endonuclease according to claim 1, wherein the DNA is from an organism.

3. The isolated type II restriction endonuclease according to claim 1, wherein the DNA is manually synthesized.

4. The isolated type II restriction endonuclease according to claim 1, wherein the type II restriction endonuclease cleaves the DNA between the fourth and fifth bases downstream from the 3' end of SEQ ID NO: 1, and in the complementary strand, between the fifth and sixth bases downstream from the 5' end of the complement of SEQ ID NO:1.

5. The isolated type II restriction endonuclease according to claim 1, wherein the type II restriction endonuclease is an enzyme derived from a microorganism.

6. The isolated type II restriction endonuclease according to claim 5, wherein the microorganism is *Helicobacter pylori*.

7. An isolated nucleic acid encoding a type II restriction endonuclease comprising the amino acid sequence of SEQ ID NO: 3.

8. The isolated nucleic acid according to claim 7, wherein the nucleic acid has the sequence of SEQ ID NO: 2.

9. The isolated nucleic acid according to claim 8, wherein the nucleic acid is isolated from *Helicobacter pylori*.

10. A vector comprising the nucleic acid according to claim 7.

11. A isolated transformed cell comprising a vector according to claim 10.

* * * * *